(12) United States Patent
Kweon et al.

(10) Patent No.: US 9,493,425 B2
(45) Date of Patent: Nov. 15, 2016

(54) METHOD FOR PREPARATION OF BENZIMIDAZOLE DERIVATIVES

(71) Applicant: CJ HEALTHCARE CORPORATION, Seoul (KR)

(72) Inventors: Jae Hong Kweon, Suwon-si (KR); Eun Sun Kim, Gwangju (KR); Seog Beom Song, Suwon-si (KR); Sung Ah Lee, Guri-si (KR); Ji Yun Lee, Seongnam-si (KR); Kwang Do Choi, Anyang-si (KR); Young Joon Park, Seoul (KR)

(73) Assignee: CJ HEALTHCARE CORPORATION, Seoul (KR)

( * ) Notice: Subject to any disclaimer, the term of this patent is extended or adjusted under 35 U.S.C. 154(b) by 0 days.

(21) Appl. No.: 14/903,793

(22) PCT Filed: Jul. 4, 2014

(86) PCT No.: PCT/KR2014/005996
§ 371 (c)(1),
(2) Date: Jan. 8, 2016

(87) PCT Pub. No.: WO2015/005615
PCT Pub. Date: Jan. 15, 2015

(65) Prior Publication Data
US 2016/0159747 A1    Jun. 9, 2016

(30) Foreign Application Priority Data

Jul. 9, 2013   (KR) .................. 10-2013-0080389
Sep. 26, 2013  (KR) .................. 10-2013-0114349

(51) Int. Cl.
*C07D 235/08*   (2006.01)

(52) U.S. Cl.
CPC .................. *C07D 235/08* (2013.01)

(58) Field of Classification Search
None
See application file for complete search history.

(56) References Cited

U.S. PATENT DOCUMENTS 5,294,631 A    3/1994  Franz et al.

FOREIGN PATENT DOCUMENTS

| WO | 97/47603 A1 | 12/1997 | |
|---|---|---|---|
| WO | 2004/054984 A1 | 7/2004 | |
| WO | 2007/072146 A1 | 6/2007 | |
| WO | WO 2009134850 A1 * | 11/2009 | ............ A61K 31/445 |

OTHER PUBLICATIONS

Webel et al., "Development of an Efficient Process Towards the Benzimidazole BYK308944: A Key Intermediate in the Synthesis of a Potassium-Competitive Acid Blocker," *Organic Process Research & Development* 14(1):142-151 (2010).

* cited by examiner

*Primary Examiner* — Michael Barker
(74) *Attorney, Agent, or Firm* — Seed IP Law Group LLP

(57) ABSTRACT

The present invention provides a method for preparing a compound with a benzimidazole structure with an excellent yield using a low-cost starting material, not requiring an additional separation process, or not using a dangerous reagent during the manufacturing process. Furthermore, the present invention also provides an intermediate and a final product produced by the preparing method.

20 Claims, No Drawings

METHOD FOR PREPARATION OF BENZIMIDAZOLE DERIVATIVES

TECHNICAL FIELD

The present invention relates to a method for preparing benzimidazole derivatives.

BACKGROUND ART

Benzimidazole has been known as a very important pharmacophore in medicinal and chemical fields. In terms of chemical structure, the compound has a fused form between a benzene ring and an imidazole ring, and has various pharmaceutical characteristics. In the 1990s, numerous benzimidazole derivatives having substituents such as fluoro and propylene were synthesized, and they were shown to have stability, bioavailability and bioactivities.

Recently, with the extremely high prevalence of resistant bacteria, compounds having the structure of benzimidazole have been used as chemotherapeutic agents for treating infections of the resistant bacteria. This is due to the capacity of inhibit the synthesis of bacterial nucleic acids and proteins due to the structure of benzimidazole, which is similar to that of purine. Oxidazol-1H-benzimidazole, as a representative compound, has been known to have antimicrobial activity and has also been reported to have inhibitory activity against fungi as well.

Additionally, benzimidazole derivatives have been developed as HIV inhibitors. One representative example is tetrahydro-imidazo[4,5,1-jk][1,4]-benzodiazepin-2(1H)-one, which is an antiretroviral agent acting on a particular allosteric binding site of HIV-1 reverse transcriptase. Further, N-alkoxy-2-alkyl-benzimidazole has an $EC_{50}$ below 600 nM and shows an inhibitory activity on reverse transcriptase with excellent selectivity.

benzimidazole-based compounds having a sulfoxide group and a methylene group are known to inhibit gastric acid secretion by inhibiting a proton pump and protecting gastric mucosa. In addition, benzimidazole-based compounds are also known to have antiviral and antihypertensive effects.

Benzimidazole derivatives are also very useful in the textile industry, and are mainly used as a dye dispersant or a softening agent.

As described above, benzimidazole is a pharmacophore with extremely high applicability in the medicinal and chemical fields, and its synthesis has been developed by numerous research groups and suggested in many documents.

International Publication WO 1997/047603 describes a method of preparing benzimidazole using 2,6-dialkylphenyl as a starting material and International Publication WO 2004/054984 describes a method of preparing the same using 2-amino-3-nitrophenol. However, the above methods use high-cost intermediates and reagents in an amidation reaction, and there is difficulty in purification due to the use of a metal catalyst. Accordingly, the methods are not suitable for conventional large-scale production because they require a high manufacturing cost and the use of a silica gel for separating a certain intermediate.

Additionally, International Publication WO 2007/072146 describes a method of using carbon monoxide in the process of introducing a carbonyl group for amidation reaction. However, the reaction requires an additional reactor and there is a risk of exposure to carbon monoxide during the process.

Accordingly, the inventors of the present invention, while keeping in mind the above problems occurring in the prior art, have discovered a method for preparing benzimidazole, which has been known as a very important pharmacophore in medicinal and chemical fields, with a higher yield than those of the conventional methods and also enabling a large-scale production in industry while using conventionally-available reagents and solvents with a low manufacturing cost.

DISCLOSURE OF INVENTION

Technical Problem

An object of the present invention is to provide a method for preparing a compound with a benzimidazole structure with an excellent yield using a low-cost starting material, not requiring an additional separation process, or not using a dangerous reagent during the manufacturing process.

Another object of the present invention is to provide an intermediate and a final product produced by the preparing method.

Solution to Problem

In order to accomplish the above objects, the present invention provides a method for preparing a compound represented by the Chemical Formula 1 comprising:

1) preparing a compound represented by the Chemical Formula 10 by reacting a compound represented by the Chemical Formula 8 with a compound represented by the Chemical Formula 9; and 2) preparing the compound represented by the Chemical Formula 1 by reacting the compound represented by the Chemical Formula 10 with a compound represented by the Chemical Formula 11:

[Chemical Formula 1]

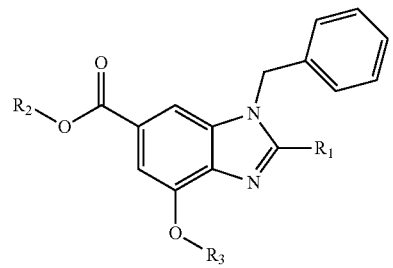

[Chemical Formula 8]

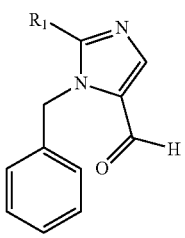

[Chemical Formula 9]

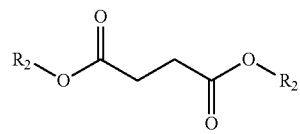

-continued

[Chemical Formula 10]

[structure: imidazole with benzyl on N, $R_1$ substituent, connected via =CH to a carbon bearing $CO_2R_2$ and $CH_2COOH$]

[Chemical Formula 11]

$R_3-C(=O)-O-C(=O)-R_3$ wherein,
$R_1$ and $R_2$ are independently $C_{1-4}$ alkyl, and
$R_3$ is $C_{1-4}$ alkyl, $C_{1-4}$haloalkyl or phenyl.

Preferably, $R_1$ and $R_2$ are independently methyl, ethyl, propyl or tert-butyl. Also, preferably, $R_3$ is methyl, trifluoromethyl or phenyl.

The method of preparing benzimidazole of the present invention, unlike the conventional methods in the related art, employs a low-cost starting material, does not require an additional separation process during the preparation, and does not use a dangerous reagent, thus being suitable for large-scale production, and also exhibiting an excellent manufacturing yield.

The step 1) is a Stobbe condensation reaction, in which a compound represented by the Chemical Formula 8 may be reacted with a compound represented by the Chemical Formula 9 to obtain a compound represented by the Chemical Formula 10.

Preferably, the step 1) may be performed in the presence of a base, and the base is preferably selected from the group consisting of potassium tert-butoxide, sodium ethoxide and sodium methoxide.

Additionally, the reaction is preferably performed using a solvent selected from the group consisting of methanol, ethanol, acetonitrile and methylene chloride.

Additionally, the reaction is preferably performed at a temperature in the range of 50° C. to 55° C. Also, in the reaction, the molar ratio between the compound represented by the Chemical Formula 8 and the compound represented by the Chemical Formula 9 is preferably in the range of 1:1 to 1:4, and more preferably is 1:1.4.

The step 2) is a cyclization reaction of benzimidazole, in which the compound represented by the Chemical Formula 10 may be reacted with a compound represented by the Chemical Formula 11 to obtain the compound represented by the Chemical Formula 1.

Preferably, the step 2) is performed using acetonitrile as a solvent.

Additionally, the reaction is preferably performed at a temperature in the range of 80° C. to 85° C. Also, in the reaction, the molar ratio between the compound represented by the Chemical Formula 10 and the compound represented by the Chemical Formula 11 is preferably in the range of 1:1 to 1:4, and more preferably is 1:2.8.

In the preparation method described above, the compound represented by the Chemical Formula 8 may be prepared by a method comprising:

a) preparing a compound represented by the Chemical Formula 4 by reacting a compound represented by the Chemical Formula 2 with a compound represented by the Chemical Formula 3;

b) preparing a compound represented by the Chemical Formula 6 by reacting the compound represented by the Chemical Formula 4 with a compound represented by the Chemical Formula 5 below; and c) preparing the compound represented by the Chemical Formula 8 by reacting the compound represented by the Chemical Formula 6 with a compound represented by the Chemical Formula 7:

[Chemical Formula 2] $R_1-C\equiv N$

[Chemical Formula 3] $R_4-OH$

[Chemical Formula 4] $R_1-C(=NH_2^+)-O-R_4$

[Chemical Formula 5] benzylamine ($PhCH_2-NH_2$)

[Chemical Formula 6] $R_1-C(=NH_2^+)-NH-CH_2Ph$

[Chemical Formula 7] [structure: cyclohexyloxy vinyl bromide with two CHO-type groups; 2-bromo-3-(cyclohexyloxy)acrolein type]

wherein,
$R_1$ is $C_{1-4}$ alkyl, and
$R_4$ is $C_{1-4}$alkyl.

Preferably, $R_1$ is methyl, ethyl, propyl or tert-butyl. Also, preferably, $R_4$ is methyl or ethyl.

The step a), a Pinner reaction, is a hydrolysis reaction of nitrile groups, in which a compound represented by the Chemical Formula 4 is obtained by reacting a compound represented by the Chemical Formula 2 with a compound represented by the Chemical Formula 3. Preferably, the reaction is performed under acidic conditions, and thus hydrochloric acid, bromic acid or acetic acid is preferably added in the reaction. Additionally, a material that can produce an acidic material during the reaction may be added. For example, it is possible to add acetyl chloride in the reaction thereby producing hydrochloric acid.

Preferably, the reaction may be performed at a temperature in the range of −10° C. to 0° C. Additionally, in the reaction, the molar ratio between the compound represented by the Chemical Formula 2 and the compound represented by the Chemical Formula 3 is preferably in the range of 1:1 to 1:4, and more preferably is 1:2.4.

The step b) is a reaction for introducing a benzyl group, in which a compound represented by the Chemical Formula 6 is obtained by reacting the compound represented by the Chemical Formula 4 with a compound represented by the Chemical Formula 5.

Preferably, the reaction is performed using methanol or ethanol as a solvent.

Additionally, the reaction is preferably performed at a temperature in the range of 23° C. to 25° C. Also, in the reaction, the molar ratio between the compound represented by the Chemical Formula 4 and the compound represented by the Chemical Formula 5 is preferably in the range of 1:1 to 1:4, and more preferably is 1:1.

The step c) is a cyclization reaction of imidazole, in which a compound represented by the Chemical Formula 8 is obtained by reacting the compound represented by the Chemical Formula 6 with a compound represented by the Chemical Formula 7.

Preferably, the reaction is performed in the presence of a base, which is more preferably selected from the group consisting of potassium carbonate, triethylamine, sodium hydroxide and diisopropylethylamine, and most preferably potassium carbonate.

Additionally, the reaction is preferably performed using a solvent selected from the group consisting of methanol, ethanol, isopropanol, methylene chloride, chloroform, water and a mixed solution thereof, and most preferably a mixed solution of methylene chloride and water.

Additionally, the reaction is preferably performed at a temperature of in the range of 40° C. to 45° C. (reflux). Also, in the reaction, the molar ratio between the compound represented by the Chemical Formula 6 and the compound represented by the Chemical Formula 7 is preferably in the range of 1:0.5 to 1:4, and more preferably is 1:0.93.

Furthermore, the present invention provides a method of preparing a compound represented by the Chemical Formula 1-1 by reacting a compound represented by the Chemical Formula 1 in the presence of a base selected from potassium carbonate or sodium bicarbonate:

[Chemical Formula 1-1]

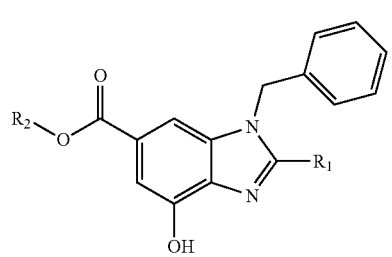

wherein, $R_1$ and $R_2$ are independently $C_{1-4}$ alkyl, and preferably methyl, ethyl, propyl or tert-butyl.

Preferably, the reaction is performed using a solvent selected from the group consisting of methanol, ethanol, water and a mixed solution thereof.

Additionally, the reaction is preferably performed at a temperature of in the range of 23° C. to 25° C. Also, in the reaction, the molar ratio between the compound represented by the Chemical Formula 1 and the base is preferably in the range of 1:1 to 1:4, and more preferably is 1:1.4.

Furthermore, the present invention provides a method of preparing a compound represented by the Chemical Formula 1-2 by reacting a compound represented by the Chemical Formula 1 in the presence of a base selected from sodium hydroxide or potassium hydroxide:

[Chemical Formula 1-2]

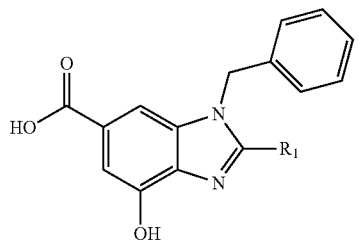

wherein, $R_1$ is $C_{1-4}$ alkyl, and preferably, methyl, ethyl, propyl or tert-butyl.

Preferably, the reaction is performed using a solvent selected from the group consisting of methanol, ethanol, water and a mixed solution thereof.

Additionally, the reaction is preferably performed at a temperature of in the range of 70° C. to 80° C. Also, in the reaction, the molar ratio between the compound represented by the Chemical Formula 1 and the base is preferably in the range of 1:1 to 1:10, and more preferably is 1:5.

Furthermore, the present invention provides a method of preparing a compound represented by the Chemical Formula 1-3 by reacting a compound represented by the Chemical Formula 1-2 with dimethylamine in the presence of thionyl chloride:

[Chemical Formula 1-3]

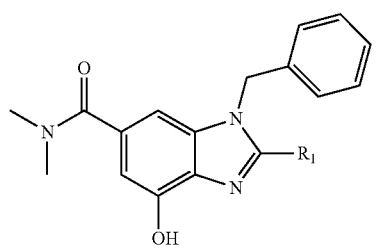

wherein $R_1$ is a $C_{1-4}$ alkyl, and preferably, methyl, ethyl, propyl or tert-butyl.

Preferably, the reaction is performed in a two-step process. First, a chloro group is introduced into the compound represented by the Chemical Formula 1-2 using thionyl chloride. Preferably, acetonitrile is used as a solvent, and the reaction is performed at 80° C. Then, an amine group is introduced via amidation reaction. Here, the amine is dimethylamine, and its salt (e.g., hydrochloride) may be used as well. The reaction is preferably performed at 0° C.

Additionally, in the reaction, the molar ratio between the compound represented by the Chemical Formula 1-2 and the amine is preferably in the range of 1:1 to 1:1.8, and more preferably is 1:1.8.

Furthermore, the present invention provides compounds represented by the Chemical Formula 1, the Chemical Formula 1-1, the Chemical Formula 1-2, or the Chemical Formula 1-3 produced by the methods described above:

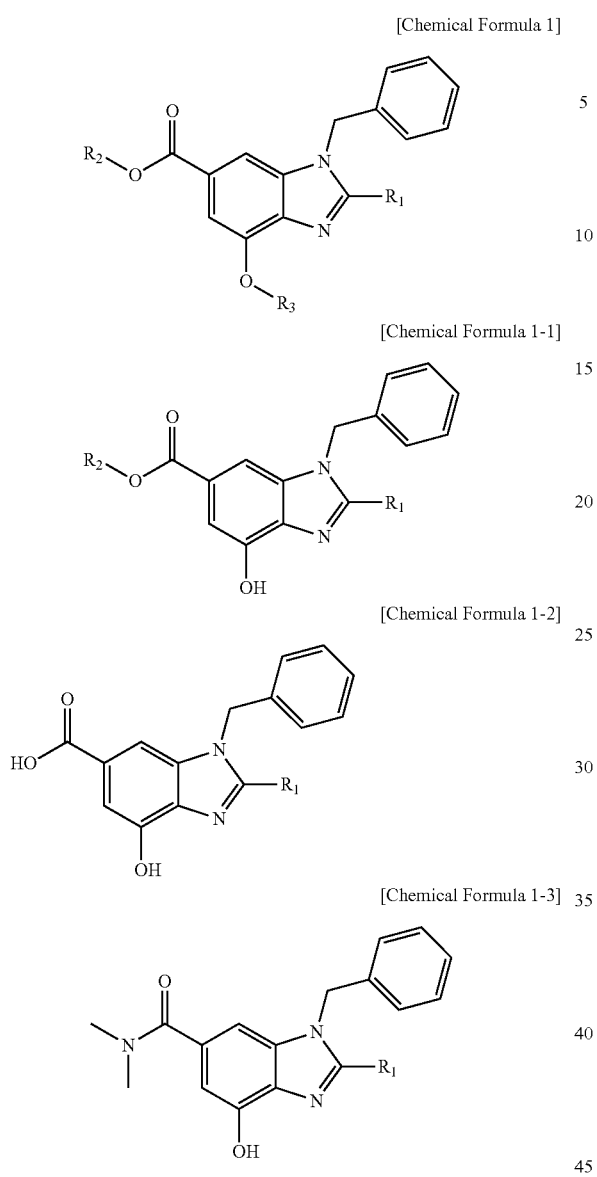

[Chemical Formula 1]
[Chemical Formula 1-1]
[Chemical Formula 1-2]
[Chemical Formula 1-3]

wherein, $R_1$, $R_2$ and $R_3$ are the same as defined above.

The representative examples of the compounds represented by the Chemical Formula 1, the Chemical Formula 1-1, the Chemical Formula 1-2, or the Chemical Formula 1-3 are as follows.

1) ethyl 4-acetoxy-1-benzyl-2-methyl-1H-benzo[d]imidazole-6-carboxylate,
2) ethyl 4-acetoxy-1-benzyl-2-ethyl-1H-benzo[d]imidazole-6-carboxylate,
3) ethyl 4-acetoxy-1-benzyl-2-tert-butyl-1H-benzo[d]imidazole-6-carboxylate,
4) ethyl 4-trifloromethoxy-1-benzyl-2-methyl-1H-benzo[d]imidazole-6-carboxylate,
5) ethyl 4-benzoyloxy-1-benzyl-2-methyl-1H-benzo[d]imidazole-6-carboxylate,
6) ethyl 1-benzyl-4-hydroxy-2-methyl-1H-benzo[d]imidazole-6-carboxylate,
7) ethyl 1-benzyl-4-hydroxy-2-ethyl-1H-benzo[d]imidazole-6-carboxylate,
8) ethyl 1-benzyl-4-hydroxy-2-tert-butyl-1H-benzo[d]imidazole-6-carboxylate,
9) 1-benzyl-4-hydroxy-2-methyl-1H-benzo[d]imidazole-6-carboxylic acid, and
10) 1-benzyl-4-hydroxy-N,N,2-trimethyl-1H-benzo[d]imidazole-6-carboxyamide.

Advantageous Effects of Invention

The method of preparing a compound having a benzimidazole structure of the present invention, unlike the conventional methods, uses a low-cost starting material, does not require an additional separation process during the manufacturing process, and does not use a dangerous reagent thus being advantageous for a large-scale production, and also has an excellent manufacturing yield.

Additionally, an intermediate and a final product produced by the preparing method of the present invention may be used for preparing other compounds having a benzimidazole structure, and in particular, utilized as an intermediate for preparing compounds which can be used for antibacterial agent, antiulcer agent or antiinflammatory therapeutic agents.

MODE FOR THE INVENTION

The present invention will be described in detail herein below with reference to the accompanying examples and experimental examples. However, the examples and experimental examples are given only for exemplary purposes and should not be construed as limiting the scope of the present invention.

Example 1

Step a

1) Example 1-1

Preparation of methyl acetimidate hydrochloride

To a reactor were added 1.6 kg of acetonitrile and 2.4 kg of methanol, and the reactor was cooled to −10° C. Acetyl chloride in the amount of 3.67 kg was slowly added thereto and the mixture was stirred at 0° C. for 12 hours. While stirring, the internal temperature of the reactor was maintained at 0° C. Upon termination of the reaction, the solvent was removed at 45° C. under reduced pressure. To the reaction mixture was added 11.8 kg of tert-butyl methyl ether and the mixture was stirred at 0° C. for 3 hours. The resulting solid was filtered and vacuum-dried at 40° C. to obtain 4.1 kg of methyl acetimidate hydrochloride (yield: 95%).

$^1$H-NMR (400 MHz, DMSO-$d_6$): 11.7 (s, 2H), 4.07 (s, 3H), 2.38 (s, 3H)

2) Example 1-2

Preparation of ethyl acetimidate hydrochloride

To a reactor were added 1.6 kg of acetonitrile and 4.3 kg of ethanol and the reactor was cooled to −10° C. Acetyl chloride in the amount of 3.67 kg was slowly added thereto and the mixture was stirred at 0° C. for 12 hours. While stiffing, the internal temperature of the reactor was maintained at 0° C. Upon termination of the reaction, the solvent was removed at 45° C. under reduced pressure. To the reaction mixture was added 11.8 kg of tert-butyl methyl ether and the mixture was stirred at 0° C. for 3 hours. The resulting solid was filtered and vacuum-dried at 40° C. to obtain 4.58 kg of ethyl acetimidate hydrochloride (yield: 95%).

$^1$H-NMR (400 MHz, DMSO-d$_6$): 11.7 (s, 2H), 4.26 (q, 2H), 2.38 (s, 3H), 1.36 (t, 3H)

3) Example 1-3

Preparation of tert-butyl acetimidate hydrochloride

To a reactor were added 1.6 kg of acetonitrile and 6.93 kg of tert-butanol and the reactor was cooled to −10° C. Acetyl chloride in the amount of 3.67 kg was slowly added thereto and the mixture was stirred at 0° C. for 12 hours. While stiffing, the internal temperature of the reactor was maintained at 0° C. Upon termination of the reaction, the solvent was removed at 45° C. under reduced pressure. To the reaction mixture was added 11.8 kg of tert-butyl methyl ether and the mixture was stirred at 0° C. for 3 hours. The resulting solid was filtered and vacuum-dried at 40° C. to obtain 5.32 kg of tert-butyl acetimidate hydrochloride (yield: 90%).

$^1$H-NMR (400 MHz, DMSO-d$_6$): 11.7 (s, 2H), 2.38 (s, 3H), 1.2 (s, 9H)

4) Example 1-4

Preparation of methyl propionimidate hydrochloride

To a reactor were added 1.6 kg of propionitrile and 2.23 kg of methanol and the reactor was cooled to −10° C. Acetyl chloride in the amount of 2.74 kg was slowly added thereto and the mixture was stirred at 0° C. for 12 hours. While stiffing, the internal temperature of the reactor was maintained at 0° C. Upon termination of the reaction, the solvent was removed at 45° C. under reduced pressure. To the reaction mixture was added 11.8 kg of tert-butyl methyl ether and the mixture was stirred at 0° C. for 3 hours. The resulting solid was filtered and vacuum-dried at 40° C. to obtain 3.41 kg of methyl propionimidate hydrochloride (yield: 95%).

$^1$H-NMR (400 MHz, DMSO-d$_6$): 11.7 (s, 2H), 4.07 (s, 3H), 1.57 (q, 2H), 0.96 (t, 3H)

5) Example 1-5

Preparation of methyl trimethylacetimidate hydrochloride

To a reactor were added 1.6 kg of trimethylacetonitrile and 1.48 kg of methanol and the reactor was cooled to −10° C. Acetyl chloride in the amount of 1.81 kg was slowly added thereto and the mixture was stirred at 0° C. for 12 hours. While stirring, the internal temperature of the reactor was maintained at 0° C. Upon termination of the reaction, the solvent was removed at 45° C. under reduced pressure. To the reaction mixture was added 11.8 kg of tert-butyl methyl ether and the mixture was stirred at 0° C. for 3 hours. The resulting solid was filtered and vacuum-dried at 40° C. to obtain 2.63 kg of methyl trimethylacetimidate hydrochloride (yield: 90%).

$^1$H-NMR (400 MHz, DMSO-d$_6$): 11.7 (s, 2H), 4.07 (s, 3H), 1.0 (s, 9H)

Example 2

Step b

1) Example 2-1

Preparation of N-benzylacetimidamide hydrochloride

To a reactor were added 3.97 kg of benzylamine and 31.4 kg of methanol. Then, 4.05 kg of methyl acetimidate hydrochloride prepared in Example 1-1 was added thereto and the mixture was stirred for 3 hours. After removing the solvent at 40° C. under reduced pressure, 31.4 kg of acetone was added dropwise to the reaction mixture and the mixture was stirred for 5 hours. The resulting solid was filtered, washed with 10 kg of acetone, and vacuum-dried at 40° C. for 12 hours to obtain 6.5 kg of N-benzylacetimidamide hydrochloride (yield: 95%).

$^1$H-NMR (400 MHz, DMSO-d$_6$): 10.10 (s, 1H), 9.50 (s, 1H), 7.30 (m, 5H), 4.59 (m, 2H), 2.31 (m, 3H)

2) Example 2-2

Preparation of N-benzylpropionimidamide hydrochloride

To a reactor were added 3.97 kg of benzylamine and 31.4 kg of methanol. Then, 4.58 kg of methyl propionimidate hydrochloride prepared in Example 1-4 was added thereto and the mixture was stirred for 3 hours. After removing the solvent at 40° C. under reduced pressure, 31.4 kg of acetone was added dropwise to the reaction mixture and the mixture was stirred for 5 hours. The resulting solid was filtered, washed with 10 kg of acetone, and vacuum-dried at 40° C. for 12 hours to obtain 6.99 kg of N-benzylpropionimidamide hydrochloride (yield: 95%).

$^1$H-NMR (400 MHz, DMSO-d$_6$): 10.10 (s, 1H), 9.50 (s, 1H), 7.30 (m, 5H), 4.59 (m, 2H), 2.70 (q, 2H), 1.20 (t, 3H)

3) Example 2-3

Preparation of N-benzylpivalimidamide hydrochloride

To a reactor were added 3.97 kg of benzylamine and 31.4 kg of methanol. Then, 5.60 kg of methyl trimethylacetimidate hydrochloride prepared in Example 1-5 was added thereto and the mixture was stirred for 3 hours. After removing the solvent at 40° C. under reduced pressure, 31.4 kg of acetone was added dropwise to the reaction mixture and the mixture was stirred for 5 hours. The resulting solid was filtered, washed with 10 kg of acetone, and vacuum-dried at 40° C. for 12 hours to obtain 7.98 kg of N-benzylpivalimidamide hydrochloride (yield: 95%).

$^1$H-NMR (400 MHz, DMSO-d$_6$): 10.10 (s, 1H), 9.50 (s, 1H), 7.30 (m, 5H), 4.59 (m, 2H), 1.26 (s, 9H)

Example 3

Step c

1) Example 3-1

Preparation of 1-benzyl-2-methyl-1H-imidazole-carbaldehyde

To a reactor were added 6.5 kg of N-benzylacetimidamide hydrochloride prepared in Example 2-1 and 9.72 kg of potassium carbonate. Then, 76.8 kg of methylene chloride and 7.22 kg of water were further added thereto, and the mixture was stirred for 30 minutes. After adding 7.63 kg of (E)-2-bromo-3-(cyclohexyloxy)acrylaldehyde to the mixture, the temperature of the reactor was increased to 40° C., and the mixture was stirred for 5 hours while maintaining the temperature. The reactants were dried at 40° C. under reduced pressure. Then, 48.1 kg of tert-butyl methyl ether was added to the reactor, stirred for 30 minutes and filtered through diatomaceous earth, and washed with 48.1 kg of tert-butyl methyl ether. To the resulting organic layer was added 65 kg of water, and the mixture was adjusted to pH 5.5 using a concentrated HCl. Then, the organic layer was separated, and 48.1 kg of tert-butyl methyl ether was added to the aqueous layer, and the mixture was stirred for 30 minutes. Then, the organic layer was separated, dried using magnesium sulfate, filtered, and dried at 40° C. under reduced pressure to obtain 6.34 kg of 1-benzyl-2-methyl-1H-imidazole-carbaldehyde (yield: 90%).

$^1$H-NMR (400 MHz, DMSO-d$_6$): 9.64 (s, 1H), 7.87 (s, 1H), 7.31 (m, 5H), 5.56 (s, 2H), 2.33 (m, 3H)

2) Example 3-2

Preparation of
1-benzyl-2-ethyl-1H-imidazole-5-carbaldehyde

To a reactor were added 6.99 kg of N-benzylpropionimidamide hydrochloride prepared in Example 2-2 and 9.72 kg of potassium carbonate. Then, 76.8 kg of methylene chloride and 7.22 kg of water were further added thereto, and the mixture was stirred for 30 minutes. After adding 7.63 kg of (E)-2-bromo-3-(cyclohexyloxy)acrylaldehyde to the mixture, the temperature of the reactor was increased to 40° C., and the mixture was stirred for 5 hours while maintaining the temperature. The reactants were dried at 40° C. under reduced pressure. Then, 48.1 kg of tert-butyl methyl ether was added to the reactor, stirred for 30 minutes and filtered through diatomaceous earth, and washed with 48.1 kg of tert-butyl methyl ether. To the resulting organic layer was added 65 kg of water, and the mixture was adjusted to pH 5.5 using a concentrated HCl. Then, the organic layer was separated, and 48.1 kg of tert-butyl methyl ether was added to the aqueous layer, and the mixture was stirred for 30 minutes. Then, the organic layer was separated, dried using magnesium sulfate, filtered, and dried at 40° C. under reduced pressure to obtain 6.78 kg of 1-benzyl-2-ethyl-1H-imidazole-5-carbaldehyde (yield: 90%).

$^1$H-NMR (400 MHz, DMSO-d$_6$): 9.64 (s, 1H), 7.87 (s, 1H), 7.31 (m, 5H), 5.56 (s, 2H), 2.85 (q, 2H), 1.25 (t, 3H)

3) Example 3-3

Preparation of 1-benzyl-2-(tert-butyl)-1H-imidazole-5-carbaldehyde

To a reactor were added 7.98 kg of N-benzylpivalimidamide hydrochloride prepared in Example 2-3 and 9.72 kg of potassium carbonate. Then, 76.8 kg of methylene chloride and 7.22 kg of water were further added thereto, and the mixture was stirred for 30 minutes. After adding 7.63 kg of (E)-2-bromo-3-(cyclohexyloxy)acrylaldehyde to the mixture, the temperature of the reactor was increased to 40° C., and the mixture was stirred for 5 hours while maintaining the temperature. The reactants were dried at 40° C. under reduced pressure. Then, 48.1 kg of tert-butyl methyl ether was added to the reactor, stirred for 30 minutes and filtered through diatomaceous earth, and washed with 48.1 kg of tert-butyl methyl ether. To the resulting organic layer was added 65 kg of water, and the mixture was adjusted to pH 5.5 using a concentrated HCl. Then, the organic layer was separated, and 48.1 kg of tert-butyl methyl ether was added to the aqueous layer, and the mixture was stirred for 30 minutes. Then, the organic layer was separated, dried using magnesium sulfate, filtered, and dried at 40° C. under reduced pressure to obtain 7.67 kg of 1-benzyl-2-(tert-butyl)-1H-imidazole-5-carbaldehyde (yield: 90%).

$^1$H-NMR (400 MHz, DMSO-d$_6$): 9.64 (s, 1H), 7.87 (s, 1H), 7.31 (m, 5H), 5.56 (s, 2H), 1.26 (s, 9H)

Example 4

Step 1

1) Example 4-1

Preparation of (E)-4-(1-benzyl-2-methyl-1H-imidazole-5-yl)-3-(ethoxycarbonyl)but-3-enoic acid To a reactor were added 3.02 kg of sodium ethoxide and dissolved by adding 25 kg of ethanol. Then, 7.72 kg of diethyl succinate was added thereto and the temperature of the reactor was increased to 55° C. Then, 6.34 kg of 1-benzyl-2-methyl-1H-imidazole-carbaldehyde prepared in Example 3-1 was dissolved in 25 kg of ethanol and added to the reactor for 3 hours. Upon termination of the reaction, ethanol was removed at 50° C. under reduced pressure. To the reactor was added 168 kg of dichloromethane and 63 kg of water and the mixture was adjusted to pH 5.5 using a concentrated HCl. Then, the mixture was stirred for 30 minutes to separate an organic layer. To the aqueous layer was added 84.3 kg of dichloromethane and the mixture was stirred for 30 minutes. The resulting organic layer was separated, dried using magnesium sulfate, filtered, and dried at 40° C. under reduced pressure. Then, 20 kg of methyl ethyl ketone was added thereto, and the mixture was stirred for 30 minutes and dried at 50° C. under reduced pressure. The resultant was added with 51 kg of methyl ethyl ketone and stirred for 3 hours. The resulting precipitated solid was filtered, washed with 10 kg of methyl ethyl ketone, vacuum-dried at 40° C. for 12 hours to obtain 3.64 kg of (E)-4-(1-benzyl-2-methyl-1H-imidazole-5-yl)-3-(ethoxycarbonyl) but-3-enoic acid (yield: 35%).

$^1$H-NMR (400 MHz, DMSO-d$_6$): 11.0 (s, 1H), 7.30-7.20 (m, 5H), 7.58 (s, 1H), 5.46 (m, 2H), 4.20 (q, 2H), 3.56 (s, 2H), 2.50 (s, 3H), 1.29 (t, 3H)

2) Example 4-2

Preparation of (E)-4-(1-benzyl-2-ethyl-1H-imidazole-5-yl)-3-(ethoxycarbonyl)but-3-enoic acid To a reactor were added 3.02 kg of sodium ethoxide and dissolved by adding 27 kg of methanol. Then, 7.72 kg of diethyl succinate was added thereto and the temperature of the reactor was increased to 55° C. Then, 6.78 kg of 1-benzyl-2-ethyl-1H-imidazole-5-carbaldehyde prepared in Example 3-2 was dissolved in 27 kg of methanol and added to the reactor for 3 hours. Upon termination of the reaction, ethanol was removed at 50° C. under reduced pressure. To the reactor was added 180 kg of dichloromethane and 68 kg of water and the mixture was adjusted to pH 5.5 using a concentrated HCl. Then, the mixture was stirred for 30 minutes to separate an organic layer. To the aqueous layer was added 90.1 kg of dichloromethane and the mixture was stirred for 30 minutes. The resulting organic layer was separated, dried using magnesium sulfate, filtered, and dried at 40° C. under reduced pressure. Then, 20 kg of methyl ethyl ketone was added thereto, and the mixture was stirred for 30 minutes and dried at 50° C. under reduced pressure. The resultant was added with 55 kg of methyl ethyl ketone and stirred for 3 hours. The resulting precipitated solid was filtered, washed with 10 kg of methyl ethyl ketone, vacuum-dried at 40° C. for 12 hours to obtain 3.79 kg of (E)-4-(1-benzyl-2-ethyl-1H-imidazole-5-yl)-3-(ethoxycarbonyl)but-3-enoic acid (yield: 35%).

$^1$H-NMR (400 MHz, DMSO-$d_6$): 11.0 (s, 1H), 7.30-7.20 (m, 5H), 7.58 (s, 1H), 5.46 (m, 2H), 4.20 (q, 2H), 3.56 (s, 2H), 2.85 (q, 2H), 1.29 (t, 3H), 1.25 (t, 3H)

3) Example 4-3

Preparation of (E)-4-(1-benzyl-2-(tert-butyl)-1H-imidazole-5-yl)-3-(ethoxycarbonyl)but-3-enoic acid To a reactor were added 3.02 kg of sodium ethoxide and dissolved by adding 30 kg of ethanol. Then, 7.72 kg of diethyl succinate was added thereto and the temperature of the reactor was increased to 55° C. Then, 7.67 kg of 1-benzyl-2-tert-butyl-1H-imidazole-5-carbaldehyde prepared in Example 3-3 was dissolved in 30 kg of ethanol and added to the reactor for 3 hours. Upon termination of the reaction, ethanol was removed at 50° C. under reduced pressure. To the reactor was added 204 kg of dichloromethane and 77 kg of water and the mixture was adjusted to pH 5.5 using a concentrated HCl. Then, the mixture was stirred for 30 minutes to separate an organic layer. To the aqueous layer was added 102 kg of dichloromethane and the mixture was stirred for 30 minutes. The resulting organic layer was separated, dried using magnesium sulfate, filtered, and dried at 40° C. under reduced pressure. Then, 20 kg of methyl ethyl ketone was added thereto, and the mixture was stirred for 30 minutes and dried at 50° C. under reduced pressure. The resultant was added with 62 kg of methyl ethyl ketone and stirred for 3 hours. The resulting precipitated solid was filtered, washed with 10 kg of methyl ethyl ketone, vacuum-dried at 40° C. for 12 hours to obtain 4.10 kg of (E)-4-(1-benzyl-2-(tert-butyl)-1H-imidazole-5-yl)-3-(ethoxycarbonyl)but-3-enoic acid (yield: 35%).

$^1$H-NMR (400 MHz, DMSO-$d_6$): 11.0 (s, 1H), 7.30~7.20 (m, 5H), 7.58 (s, 1H), 5.46 (m, 2H), 4.20 (q, 2H), 3.56 (s, 2H), 1.29 (t, 3H), 1.25 (s, 9H)

4) Example 4-4

Preparation of (E)-4-(1-benzyl-2-methyl-1H-imidazole-5-yl)-3-(methoxycarbonyl)but-3-enoic acid To a reactor were added 2.39 kg of sodium methoxide and dissolved by adding 26 kg of methanol. Then, 6.48 kg of dimethyl succinate was added thereto and the temperature of the reactor was increased to 55° C. Then, 6.34 kg of 1-benzyl-2-methyl-1H-imidazole-carbaldehyde prepared in Example 3-1 was dissolved in 26 kg of methanol and added to the reactor for 3 hours. Upon termination of the reaction, methanol was removed at 50° C. under reduced pressure. To the reactor was added 168 kg of dichloromethane and 63 kg of water and the mixture was adjusted to pH 5.5 using a concentrated HCl. Then, the mixture was stirred for 30 minutes to separate an organic layer. To the aqueous layer was added 84.3 kg of dichloromethane and the mixture was stirred for 30 minutes. The resulting organic layer was separated, dried using magnesium sulfate, filtered, and dried at 40° C. under reduced pressure. Then, 20 kg of methyl ethyl ketone was added thereto, and the mixture was stirred for 30 minutes and dried at 50° C. under reduced pressure. The resultant was added with 52 kg of methyl ethyl ketone and stirred for 3 hours. The resulting precipitated solid was filtered, washed with 10 kg of methyl ethyl ketone, vacuum-dried at 40° C. for 12 hours to obtain 3.46 kg of (E)-4-(1-benzyl-2-methyl-1H-imidazole-5-yl)-3-(methoxycarbonyl)but-3-enoic acid (yield: 34%).

$^1$H-NMR (400 MHz, DMSO-$d_6$): 11.0 (s, 1H), 7.30-7.20 (m, 5H), 7.58 (s, 1H), 6.90 (s, 1H), 5.46 (m, 2H), 3.77 (s, 3H), 3.56 (s, 2H), 2.50 (s, 3H)

5) Example 4-5

Preparation of (E)-4-(1-benzyl-2-ethyl-1H-imidazole-5-yl)-3-(methoxycarbonyl)but-3-enoic acid To a reactor were added 2.39 kg of sodium methoxide and dissolved by adding 27 kg of methanol. Then, 6.48 kg of dimethyl succinate was added thereto and the temperature of the reactor was increased to 55° C. Then, 6.78 kg of 1-benzyl-2-ethyl-1H-imidazole-5-carbaldehyde prepared in Example 3-2 was dissolved in 27 kg of methanol and added to the reactor for 3 hours. Upon termination of the reaction, methanol was removed at 50° C. under reduced pressure. To the reactor was added 180 kg of dichloromethane and 68 kg of water and the mixture was adjusted to pH 5.5 using a concentrated HCl. Then, the mixture was stirred for 30 minutes to separate an organic layer. To the aqueous layer was added 90.1 kg of dichloromethane and the mixture was stirred for 30 minutes. The resulting organic layer was separated, dried using magnesium sulfate, filtered, and dried at 40° C. under reduced pressure. Then, 20 kg of methyl ethyl ketone was added thereto, and the mixture was stirred for 30 minutes and dried at 50° C. under reduced pressure. The resultant was added with 55 kg of methyl ethyl ketone and stirred for 3 hours. The resulting precipitated solid was filtered, washed with 10 kg of methyl ethyl ketone, vacuum-dried at 40° C. for 12 hours to obtain 3.74 kg of (E)-4-(1-benzyl-2-ethyl-1H-imidazole-5-yl)-3-(methoxycarbonyl)but-3-enoic acid (yield: 36%).

$^1$H-NMR (400 MHz, DMSO-$d_6$): 11.0 (s, 1H), 7.30-7.20 (m, 5H), 7.58 (s, 1H), 6.90 (s, 1H), 5.46 (m, 2H), 3.77 (s, 3H), 3.56 (s, 2H), 2.85 (q, 2H), 1.29 (t, 3H)

6) Example 4-6

Preparation of (E)-4-(1-benzyl-2-(tert-butyl)-1H-imidazole-5-yl)-3-(methoxycarbonyl)but-3-enoic acid To a reactor were added 2.39 kg of sodium methoxide and dissolved by adding 30 kg of methanol. Then, 6.48 kg of dimethyl succinate was added thereto and the temperature of the reactor was increased to 55° C. Then, 7.67 kg of 1-benzyl-2-tert-butyl-1H-imidazole-carbaldehyde prepared in Example 3-3 was dissolved in 30 kg of methanol and added to the reactor for 3 hours. Upon termination of the reaction, methanol was removed at 50° C. under reduced pressure. To the reactor was added 204 kg of dichloromethane and 77 kg of water and the mixture was adjusted to pH 5.5 using a concentrated HCl. Then, the mixture was stirred for 30 minutes to separate an organic layer. To the aqueous layer was added 102 kg of dichloromethane and the mixture was stirred for 30 minutes. The resulting organic layer was separated, dried using magnesium sulfate, filtered, and dried at 40° C. under reduced pressure. Then, 20 kg of methyl ethyl ketone was added thereto, and the mixture was stirred for 30 minutes and dried at 50° C. under reduced pressure. The resultant was added with 62 kg of methyl ethyl ketone and stirred for 3 hours. The resulting precipitated solid was filtered, washed with 10 kg of methyl ethyl ketone, vacuum-dried at 40° C. for 12 hours to obtain 3.95 kg of (E)-4-(1-benzyl-2-(tert-butyl)-1H-imidazole-5-yl)-3-(methoxycarbonyl)but-3-enoic acid (yield: 35%).

$^1$H-NMR (400 MHz, DMSO-$d_6$): 11.0 (s, 1H), 7.30-7.20 (m, 5H), 7.58 (s, 1H), 6.92 (s, 1H), 5.45 (m, 2H), 3.56 (s, 2H), 1.29 (t, 3H), 1.20 (s, 9H)

7) Example 4-7

Preparation of (E)-4-(1-benzyl-2-methyl-1H-imidazole-5-yl)-3-(tert-butoxycarbonyl)but-3-enoic acid To a reactor were added 3.55 kg of potassium tert-butoxide and dissolved by adding 25 kg of tert-butanol. Then, 8.02 kg of di-tert-butyl succinate was added thereto and the temperature of the reactor was increased to 55° C. Then, 6.34 kg of 1-benzyl-2-methyl-1H-imidazole-carbaldehyde prepared in Example 3-1 was dissolved in 25 kg of tert-butanol and added to the reactor for 3 hours. Upon termination of the reaction, tert-butanol was removed at 50° C. under reduced pressure. To the reactor was added 168 kg of dichloromethane and 63 kg of water and the mixture was adjusted to pH 5.5 using a concentrated HCl. Then, the mixture was stirred for 30 minutes to separate an organic layer. To the aqueous layer was added 84.3 kg of dichloromethane and the mixture was stirred for 30 minutes. The resulting organic layer was separated, dried using magnesium sulfate, filtered, and dried at 40° C. under reduced pressure. Then, 20 kg of methyl ethyl ketone was added thereto, and the mixture was stirred for 30 minutes and dried at 50° C. under reduced pressure. The resultant was added with 52 kg of methyl ethyl ketone and stirred for 3 hours. The resulting precipitated solid was filtered, washed with 10 kg of methyl ethyl ketone, vacuum-dried at 40° C. for 12 hours to obtain 3.95 kg of (E)-4-(1-benzyl-2-methyl-1H-imidazole-5-yl)-3-(tert-butoxycarbonyl)but-3-enoic acid (yield: 35%).

$^1$H-NMR (400 MHz, DMSO-$d_6$): 11.0 (s, 1H), 7.30-7.20 (m, 5H), 7.58 (s, 1H), 6.90 (s, 1H), 5.40 (m, 2H), 3.56 (s, 2H), 2.50 (s, 3H), 1.38 (s, 9H)

8) Example 4-8

Preparation of (E)-4-(1-benzyl-2-ethyl-1H-imidazole-5-yl)-3-(tert-butoxycarbonyl)but-3-enoic acid To a reactor were added 3.55 kg of potassium tert-butoxide and dissolved by adding 25 kg of tert-butanol. Then, 8.02 kg of di-tert-butyl succinate was added thereto and the temperature of the reactor was increased to 55° C. Then, 6.78 kg of 1-benzyl-2-ethyl-1H-imidazole-5-carbaldehyde prepared in Example 3-2 was dissolved in 25 kg of tert-butanol and added to the reactor for 3 hours. Upon termination of the reaction, tert-butanol was removed at 50° C. under reduced pressure. To the reactor was added 180 kg of dichloromethane and 68 kg of water and the mixture was adjusted to pH 5.5 using a concentrated HCl. Then, the mixture was stirred for 30 minutes to separate an organic layer. To the aqueous layer was added 90.1 kg of dichloromethane and the mixture was stirred for 30 minutes. The resulting organic layer was separated, dried using magnesium sulfate, filtered, and dried at 40° C. under reduced pressure. Then, 20 kg of methyl ethyl ketone was added thereto, and the mixture was stirred for 30 minutes and dried at 50° C. under reduced pressure. The resultant was added with 55 kg of methyl ethyl ketone and stirred for 3 hours. The resulting precipitated solid was filtered, washed with 10 kg of methyl ethyl ketone, vacuum-dried at 40° C. for 12 hours to obtain 3.99 kg of (E)-4-(1-benzyl-2-ethyl-1H-imidazole-5-yl)-3-(tert-butoxycarbonyl)but-3-enoic acid (yield: 34%).

$^1$H-NMR (400 MHz, DMSO-$d_6$): 11.0 (s, 1H), 7.30-7.20 (m, 5H), 7.58 (s, 1H), 6.95 (s, 1H), 5.46 (m, 2H), 3.56 (s, 2H), 2.85 (q, 2H), 1.29 (t, 3H), 1.38 (s, 9H)

9) Example 4-9

Preparation of (E)-4-(1-benzyl-2-(tert-butyl)-1H-imidazole-5-yl)-3-(tert-butoxycarbonyl)but-3-enoic acid To a reactor were added 3.55 kg of potassium tert-butoxide and dissolved by adding 30 kg of tert-butanol. Then, 6.48 kg of di-tert-butyl succinate was added thereto and the temperature of the reactor was increased to 55° C. Then, 7.67 kg of 1-benzyl-2-tert-butyl-1H-imidazole-5-carbaldehyde prepared in Example 3-3 was dissolved in 30 kg of tert-butanol and added to the reactor for 3 hours. Upon termination of the reaction, tert-butanol was removed at 50° C. under reduced pressure. To the reactor was added 204 kg of dichloromethane and 77 kg of water and the mixture was adjusted to pH 5.5 using a concentrated HCl. Then, the mixture was stirred for 30 minutes to separate an organic layer. To the aqueous layer was added 102 kg of dichloromethane and the mixture was stirred for 30 minutes. The resulting organic layer was separated, dried using magnesium sulfate, filtered, and dried at 40° C. under reduced pressure. Then, 20 kg of methyl ethyl ketone was added thereto, and the mixture was stirred for 30 minutes and dried at 50° C. under reduced pressure. The resultant was added with 62 kg of methyl ethyl ketone and stirred for 3 hours. The resulting precipitated solid was filtered, washed with 10 kg of methyl ethyl ketone, vacuum-dried at 40° C. for 12 hours to obtain 4.42 kg of (E)-4-(1-benzyl-2-(tert-butyl)-1H-imidazole-5-yl)-3-(tert-butoxycarbonyl)but-3-enoic acid (yield: 35%).

$^1$H-NMR (400 MHz, DMSO-$d_6$): 11.0 (s, 1H), 7.30-7.20 (m, 5H), 7.58 (s, 1H), 6.91 (s, 1H), 5.42 (m, 2H), 3.56 (s, 2H), 1.39 (s, 9H), 1.25 (s, 9H)

Example 5

Step 2

1) Example 5-1

Preparation of ethyl 4-acetoxy-1-benzyl-2-methyl-1H-benzo[d]imidazole-6-carboxylate (E)-4-(1-benzyl-2-methyl-1H-imidazole-5-yl)-3-(ethoxycarbonyl)but-3-enoic acid, prepared in Example 4-1, in the amount of 3.64 kg was dissolved in 14.3 kg of acetonitrile, and the temperature of the mixture was increased to 80° C. Acetic anhydride in the amount of 3.17 kg was added thereto for 1 hour, and the mixture was stirred under reflux at the same temperature for 3 hours. The reactants were concentrated at 50° C. under reduced pressure. Toluene in the amount of 6.3 kg was added thereto and reconcentrated at 50° C. Isopropyl alcohol in the amount of 14.3 kg was added thereto and the mixture was stirred at 0° C. for 5 hours. The resulting solid was filtered and washed with isopropyl alcohol, cooled to 0° C., in the amount of 2.86 kg, and vacuum-dried at 40° C. to obtain 3.12 kg of ethyl 4-acetoxy-1-benzyl-2-methyl-1H-benzo[d]imidazole-6-carboxylate (yield: 80%).

$^1$H-NMR (400 MHz, DMSO-$d_6$): 8.10 (s, 1H), 7.61 (s, 1H), 7.40-7.15 (m, 5H), 5.59 (m, 2H), 4.31 (q, 2H), 2.61 (s, 3H), 2.48 (s, 3H), 1.35 (t, 3H)

2) Example 5-2

Preparation of ethyl 4-acetoxy-1-benzyl-2-ethyl-1H-benzo[d]imidazole-6-carboxylate (E)-4-(1-benzyl-2-ethyl-1H-imidazole-5-yl)-3-(ethoxycarbonyl)but-3-enoic acid, prepared in Example 4-2, in the amount of 3.79 kg was dissolved in 14.9 kg of acetonitrile, and the temperature of the mixture was increased to 80° C. Acetic anhydride in the amount of 3.17 kg was added thereto for 1 hour, and the mixture was stirred under reflux at the same temperature for 3 hours. The reactants were concentrated at 50° C. under reduced pressure. Toluene in the amount of 6.6 kg was added thereto and reconcentrated at 50° C. Isopropyl alcohol in the amount of 14.9 kg was added thereto and the mixture was stirred at 0° C. for 5 hours. The resulting solid was filtered and washed with isopropyl alcohol, cooled to 0° C., in the amount of 2.9 kg, and vacuum-dried at 40° C. to obtain 3.25 kg of ethyl 4-acetoxy-1-benzyl-2-ethyl-1H-benzo[d]imidazole-6-carboxylate (yield: 80%).

$^1$H-NMR (400 MHz, DMSO-$d_6$): 8.10 (s, 1H), 7.61 (s, 1H), 7.40-7.15 (m, 5H), 5.59 (m, 2H), 4.31 (q, 2H), 2.81 (q, 2H), 2.61 (s, 3H), 1.29-1.25 (m, 6H)

3) Example 5-3

Preparation of ethyl 4-acetoxy-1-benzyl-2-tert-butyl-1H-benzo[d]imidazole-6-carboxylate (E)-4-(1-benzyl-2-tert-butyl-1H-imidazole-5-yl)-3-(ethoxycarbonyl)but-3-enoic acid, prepared in Example 4-3, in the amount of 4.10 kg was dissolved in 16.1 kg of acetonitrile, and the temperature of the mixture was increased to 80° C. Acetic anhydride in the amount of 3.17 kg was added thereto for 1 hour, and the mixture was stirred under reflux at the same temperature for 3 hours. The reactants were concentrated at 50° C. under reduced pressure. Toluene in the amount of 7.1 kg was added thereto and reconcentrated at 50° C. Isopropyl alcohol in the amount of 16.1 kg was added thereto and the mixture was stirred at 0° C. for 5 hours. The resulting solid was filtered and washed with isopropyl alcohol, cooled to 0° C., in the amount of 2.86 kg, and vacuum-dried at 40° C. to obtain 3.50 kg of ethyl 4-acetoxy-1-benzyl-2-tert-butyl-1H-benzo[d]imidazole-6-carboxylate (yield: 80%).

$^1$H-NMR (400 MHz, DMSO-$d_6$): 8.10 (s, 1H), 7.61 (s, 1H), 7.40-7.15 (m, 5H), 5.59 (m, 2H), 4.31 (q, 2H), 2.61 (s, 3H), 1.38 (s, 9H), 1.29 (t, 3H)

4) Example 5-4

Preparation of ethyl 4-trifloromethoxy-1-benzyl-2-methyl-1H-benzo[d]imidazole-6-carboxylate (E)-4-(1-benzyl-2-methyl-1H-imidazole-5-yl)-3-(ethoxycarbonyl)but-3-enoic acid, prepared in Example 4-1, in the amount of 3.64 kg was dissolved in 14.3 kg of acetonitrile, and the temperature of the mixture was increased to 80° C. Trifloroacetic anhydride in the amount of 6.52 kg was added thereto for 1 hour, and the mixture was stirred under reflux at the same temperature for 3 hours. The reactants were concentrated at 50° C. under reduced pressure. Toluene in the amount of 6.3 kg was added thereto and reconcentrated at 50° C. Isopropyl alcohol in the amount of 14.3 kg was added thereto and the mixture was stirred at 0° C. for 5 hours. The resulting solid was filtered and washed with isopropyl alcohol, cooled to 0° C., in the amount of 2.86 kg, and vacuum-dried at 40° C. to obtain 3.15 kg of ethyl 4-trifloromethoxy-1-benzyl-2-methyl-1H-benzo[d]imidazole-6-carboxylate (yield: 75%).

$^1$H-NMR (400 MHz, DMSO-$d_6$): 8.10 (s, 1H), 7.61 (s, 1H), 7.40-7.15 (m, 5H), 5.59 (m, 2H), 4.31 (q, 2H), 2.61 (s, 3H), 2.48 (s, 3H), 1.35 (t, 3H)

5) Example 5-5

Preparation of ethyl 4-benzoyloxy-1-benzyl-2-methyl-1H-benzo[d]imidazole-6-carboxylate (E)-4-(1-benzyl-2-methyl-1H-imidazole-5-yl)-3-(ethoxycarbonyl)but-3-enoic acid, prepared in Example 4-1, in the amount of 3.64 kg was dissolved in 14.3 kg of acetonitrile, and the temperature of the mixture was increased to 80° C. Benzoic anhydride in the amount of 7.02 kg was added thereto for 1 hour, and the mixture was stirred under reflux at the same temperature for 3 hours. The reactants were concentrated at 50° C. under reduced pressure. Toluene in the amount of 6.3 kg was added thereto and reconcentrated at 50° C. Isopropyl alcohol in the amount of 14.3 kg was added thereto and the mixture was stirred at 0° C. for 5 hours. The resulting solid was filtered and washed with isopropyl alcohol, cooled to 0° C., in the amount of 2.86 kg, and vacuum-dried at 40° C. to obtain 3.68 kg of ethyl 4-benzoyloxy-1-benzyl-2-methyl-1H-benzo[d]imidazole-6-carboxylate (yield: 80%).

$^1$H-NMR (400 MHz, DMSO-$d_6$): 8.20 (s, 1H), 8.11 (s, 1H), 7.40-7.15 (m, 10H), 5.59 (m, 2H), 4.31 (q, 2H), 2.48 (s, 3H), 1.35 (t, 3H)

Example 6

Preparation of Compound of Chemical Formula 1-1

1) Example 6-1

Preparation of ethyl 1-benzyl-4-hydroxy-2-methyl-1H-benzo[d]imidazole-6-carboxylate Ethyl 4-acetoxy-1-benzyl-2-methyl-1H-benzo[d]imidazole-6-carboxylate, prepared in Example 5-1, in the amount of 3.12 kg was dissolved in 24.6 kg of ethanol. Then, potassium carbonate in the amount of 2.45 kg was added thereto and the mixture was stirred for 12 hours. Upon termination of the reaction, ethanol was removed at 40° C. under reduced pressure. Water in the amount of 31.2 kg was added thereto and then added with and the mixture was adjusted to pH 6.5 using a concentrated HCl. Then, the mixture was stirred for 1 hour at the same temperature and the resulting solid was filtered, washed with 30 kg of ethanol/water (1:1 volume ratio) and vacuum-dried at 40° C. for 12 hours to obtain 2.34 kg of ethyl 1-benzyl-4-hydroxy-2-methyl-1H-benzo[d]imidazole-6-carboxylate (yield: 85%).

¹H-NMR (400 MHz, DMSO-d₆): 7.55 (s, 1H), 7.36-7.15 (m, 6H), 5.59 (m, 2H), 4.31 (q, 2H), 2.52 (s, 3H), 1.45 (t, 3H)

2) Example 6-2

Preparation of ethyl 1-benzyl-4-hydroxy-2-ethyl-1H-benzo[d]imidazole-6-carboxylate Ethyl 4-acetoxy-1-benzyl-2-ethyl-1H-benzo[d]imidazole-6-carboxylate, prepared in Example 5-2, in the amount of 3.25 kg was dissolved in 25.6 kg of ethanol. Then, potassium carbonate in the amount of 2.45 kg was added thereto and the mixture was stirred for 12 hours. Upon termination of the reaction, ethanol was removed at 40° C. under reduced pressure. Water in the amount of 32.5 kg was added thereto and then added with and the mixture was adjusted to pH 6.5 using a concentrated HCl. Then, the mixture was stirred for 1 hour at the same temperature and the resulting solid was filtered, washed with 30 kg of ethanol/water (1:1 volume ratio) and vacuum-dried at 40° C. for 12 hours to obtain 2.44 kg of ethyl 1-benzyl-4-hydroxy-2-ethyl-1H-benzo[d]imidazole-6-carboxylate (yield: 85%).

¹H-NMR (400 MHz, DMSO-d₆): 7.55 (s, 1H), 7.36-7.15 (m, 6H), 5.59 (m, 2H), 4.31 (q, 2H), 2.90 (q, 2H), 1.45-1.38 (m, 6H)

3) Example 6-3

Preparation of ethyl 1-benzyl-4-hydroxy-2-tert-butyl-1H-benzo[d]imidazole-6-carboxylate Ethyl 4-acetoxy-1-benzyl-2-tert-butyl-1H-benzo[d]imidazole-6-carboxylate, prepared in Example 5-3, in the amount of 3.50 kg was dissolved in 27.6 kg of ethanol. Then, potassium carbonate in the amount of 2.45 kg was added thereto and the mixture was stirred for 12 hours. Upon termination of the reaction, ethanol was removed at 40° C. under reduced pressure. Water in the amount of 35.0 kg was added thereto and then added with and the mixture was adjusted to pH 6.5 using a concentrated HCl. Then, the mixture was stirred for 1 hour at the same temperature and the resulting solid was filtered, washed with 30 kg of ethanol/water (1:1 volume ratio) and vacuum-dried at 40° C. for 12 hours to obtain 2.50 kg of ethyl 1-benzyl-4-hydroxy-2-tert-butyl-1H-benzo[d]imidazole-6-carboxylate (yield: 80%).

¹H-NMR (400 MHz, DMSO-d₆): 7.55 (s, 1H), 7.36-7.15 (m, 6H), 5.59 (m, 2H), 4.31 (q, 2H), 1.45 (t, 3H), 1.38 (s, 9H)

Example 7

Preparation of Compound represented by Chemical Formula 1-2(1-benzyl-4-hydroxy-2-methyl-1H-benzo[d]imidazole-6-carboxylic acid)

Ethyl 4-acetoxy-1-benzyl-2-methyl-1H-benzo[d]imidazole-6-carboxylate, prepared in Example 5-1, in the amount of 3.12 kg was dissolved in 12.3 kg of ethanol, and added with 1.06 kg of sodium hydroxide dissolved in 15.6 kg of water. The temperature of the mixture was increased to 70° C., and the mixture was stirred for 12 hours. Upon termination of the reaction, the mixture was cooled to room temperature, added with 15.6 kg of water, and then adjusted to pH 4.0 using a concentrated HCl. The resultant was stirred for 1 hour at the same temperature and the resulting solid was filtered, washed with 15 kg of ethanol/water (1:1 volume ratio) and vacuum-dried at 40° C. for 12 hours to obtain 2.25 kg of 1-benzyl-4-hydroxy-2-methyl-1H-benzo[d]imidazole-6-carboxylic acid (yield: 90%)

¹H-NMR (400 MHz, DMSO-d₆): 10.21 (s, 1H), 7.85 (s, 1H), 7.55 (s, 1H), 7.36-7.15 (m, 5H), 5.59 (m, 2H), 2.52 (s, 3H)

Example 8

Preparation of Compound represented by Chemical Formula 1-3(1-benzyl-4-hydroxy-N,N,2-trimethyl-1H-benzo[d]imidazole-6-carboxyamide)

1-benzyl-4-hydroxy-2-methyl-1H-benzo[d]imidazole-6-carboxylic acid, prepared in Example 7, in the amount of 2.25 kg was dissolved in 17.7 kg of acetonitrile, and then added with 0.0276 kg of dimethylformamide. The temperature of the mixture was increased to 80° C., and added with 1.31 kg of thionyl chloride for 30 minutes. The reaction mixture was stirred for 5 hours. Upon termination of the reaction, the temperature of the mixture was cooled to 0° C., and added with 1.17 kg of dimethylamine hydrochloride. Then, 4.03 kg of triethylamine was slowly added dropwise thereto for 1 hour. The reaction temperature was increased to room temperature and the mixture was stirred for 3 hours. The reaction solvent was removed at 45° C. under reduced pressure. Water in the amount of 22.5 kg was added thereto and stirred for 12 hours. The resulting solid was filtered, washed with 6.75 kg of ethanol/water (1:2 volume ratio) and vacuum-dried at 40° C. to obtain 2.10 kg of 1-benzyl-4-hydroxy-N,N,2-trimethyl-1H-benzo[d]imidazole-6-carboxyamide of the Chemical Formula 1-3.

¹H-NMR (400 MHz, DMSO-d₆): 9.99 (s, 1H), 7.52-7.25 (m, 5H), 6.98 (s, 1H), 6.64 (s, 1H), 5.49 (s, 2H), 2.85 (s, 6H), 2.52 (s, 3H)

The invention claimed is:

1. A method for preparing benzimidazole derivatives, comprising:

1) preparing a compound represented by the Chemical Formula 10 by reacting a compound represented by the Chemical Formula 8 with a compound represented by the Chemical Formula 9; and 2) preparing a compound represented by the Chemical Formula 1 by reacting the compound represented by the Chemical Formula 10 with a compound represented by the Chemical Formula 11:

[Chemical Formula 1]

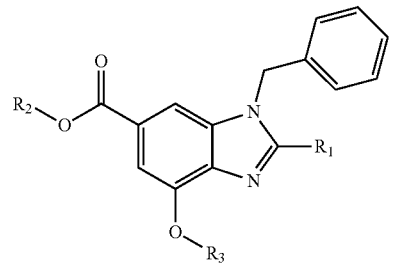

-continued

[Chemical Formula 8]

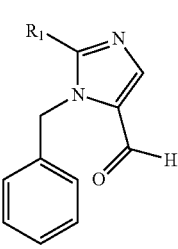

[Chemical Formula 9]

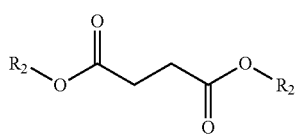

[Chemical Formula 10]

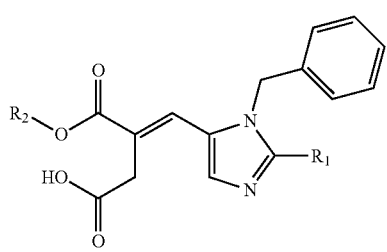

[Chemical Formula 11]

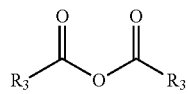

wherein, $R_1$ and $R_2$ are independently $C_{1-4}$ alkyl, and $R_3$ is $C_{1-4}$ alkyl, $C_{1-4}$ haloalkyl or phenyl.

2. A method of preparing a compound represented by the Chemical Formula 1-1 by reacting a compound represented by the Chemical Formula 1 of claim 1 in the presence of a base selected from potassium carbonate or sodium bicarbonate:

[Chemical Formula 1-1]

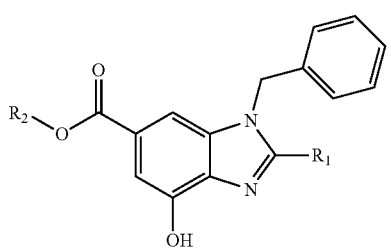

wherein, $R_1$ and $R_2$ are independently $C_{1-4}$ alkyl.

3. A method of preparing a compound represented by the Chemical Formula 1-2 by reacting a compound represented by the Chemical Formula 1 of claim 1 in the presence of a base selected from sodium hydroxide or potassium hydroxide:

[Chemical Formula 1-2]

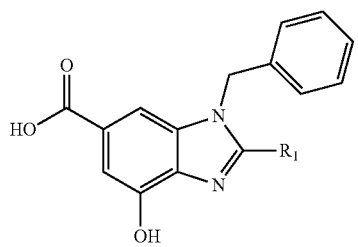

wherein, $R_1$ is $C_{1-4}$ alkyl.

4. A method of preparing a compound represented by the Chemical Formula 1-3 by reacting a compound represented by the Chemical Formula 1-2 of claim 3 with dimethylamine in the presence of thionyl chloride:

[Chemical Formula 1-3]

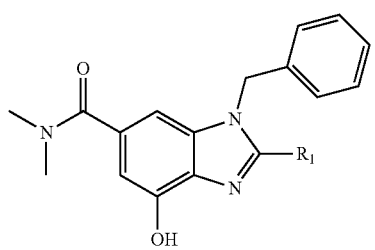

wherein, $R_1$ is $C_{1-4}$ alkyl.

5. The method of claim 1, wherein $R_1$ are independently methyl, ethyl, propyl or tert-butyl.

6. The method of claim 1, wherein $R_3$ is methyl, trifluoromethyl or phenyl.

7. The method of claim 1, wherein step 1) is performed in the presence of a base selected from the group consisting of potassium tert-butoxide, sodium ethoxide and sodium methoxide.

8. The method of claim 1, wherein step 1) is performed using a solvent selected from the group consisting of methanol, ethanol, acetonitrile and methylene chloride.

9. The method of claim 1, wherein step 2) is performed using acetonitrile as a solvent.

10. The method of claim 1, wherein the compound represented by the Chemical Formula 8 is prepared by a method comprising:

a) preparing a compound represented by the Chemical Formula 4 by reacting a compound represented by the Chemical Formula 2 with a compound represented by the Chemical Formula 3;

b) preparing a compound represented by the Chemical Formula 6 by reacting the compound represented by the Chemical Formula 4 with a compound represented by the Chemical Formula 5 below; and c) preparing the compound represented by the Chemical Formula 8 by reacting the compound represented by the Chemical Formula 6 with a compound represented by the Chemical Formula 7;

[Chemical Formula 2]

$R_1\!\!-\!\!\!\equiv\!\!\!-\!\!N$

[Chemical Formula 3]

R₄—OH

[Chemical Formula 4]

(structure: R₁-C(=NH₂⁺)-O-R₄)

[Chemical Formula 5]

(benzylamine structure)

[Chemical Formula 6]

(R₁-C(=NH₂⁺)-NH-CH₂-phenyl)

[Chemical Formula 7]

(structure: OHC-C(Br)=CH-O-cyclohexyl)

wherein,

R₁ is $C_{1-4}$ alkyl, and

R₄ is $C_{1-4}$ alkyl.

11. The method of claim 10, wherein R₁ is methyl, ethyl, propyl or tert-butyl.

12. The method of claim 10, wherein R₄ is methyl or ethyl.

13. The method of claim 10, wherein hydrochloric acid, bromic acid or acetic acid is added in step a).

14. The method of claim 10, wherein acetyl chloride is added in step a).

15. The method of claim 10, wherein step c) is performed in the presence of a base selected from the group consisting of potassium carbonate, triethylamine, sodium hydroxide and diisopropylethylamine.

16. The method of claim 3, wherein the reaction is performed using a solvent selected from the group consisting of methanol, ethanol, water and a mixed solution thereof.

17. A compound represented by the Chemical Formula 1, Chemical Formula 1-1, Chemical Formula 1-2 or Chemical Formula 1-3:

[Chemical Formula 1]

(benzimidazole structure with R₂O-C(=O)-, N-benzyl, 2-R₁, 4-OR₃)

[Chemical Formula 1-1]

(benzimidazole structure with R₂O-C(=O)-, N-benzyl, 2-R₁, 4-OH)

[Chemical Formula 1-2]

(benzimidazole structure with HOOC-, N-benzyl, 2-R₁, 4-OH)

[Chemical Formula 1-3]

(benzimidazole structure with (CH₃)₂N-C(=O)-, N-benzyl, 2-R₁, 4-OH)

wherein,

R₁ and R₂ are independently $C_{1-4}$ alkyl, and

R₃ is $C_{1-4}$ alkyl, $C_{1-4}$ haloalkyl or phenyl.

18. The compound of claim 17, wherein R₁ and R₂ are independently methyl, ethyl; propyl or tert-butyl.

19. The compound of claim 17, wherein R₃ is methyl, trifluoromethyl or phenyl.

20. The compound of claim 17, wherein the compound represented by the Chemical Formula 1, the Chemical Formula 1-1, the Chemical Formula 1-2 or the Chemical Formula 1-3 is selected from the group consisting of, 1) ethyl 4-acetoxy-1-benzyl-2-methyl-1H-benzo[d]imidazole-6-carboxylate,
2) ethyl 4-acetoxy-1-benzyl-2-ethyl-1H-benzo[d]imidazole-6-carboxylate,
3) ethyl 4-acetoxy-1-benzyl-2-tert-butyl-1H-benzo[d]imidazole-6-carboxylate,
4) ethyl 4-trifloromethoxy-1-benzyl-2-methyl-1H-benzo[d]imidazole-6-carboxylate,
5) ethyl 4-benzoyloxy-1-benzyl-2-methyl-1H-benzo[d]imidazole-6-carboxylate, 6) ethyl 1-benzyl-4-hydroxy-2-methyl-1H-benzo[d]imidazole-6-carboxylate,
7) ethyl 1-benzyl-4-hydroxy-2-ethyl-1H-benzo[d]imidazole-6-carboxylate,
8) ethyl 1-benzyl-4-hydroxy-2-tert-butyl-1H-benzo[d]imidazole-6-carboxylate,
9) 1-benzyl-4-hydroxy-2-methyl-1H-benzo[d]imidazole-6-carboxylic acid, and
10) 1-benzyl-4-hydroxy-N,N,2-trimethyl-1H-benzo[d]imidazole-6-carboxyamide.

* * * * *

UNITED STATES PATENT AND TRADEMARK OFFICE
CERTIFICATE OF CORRECTION

PATENT NO. : 9,493,425 B2  Page 1 of 1
APPLICATION NO. : 14/903793
DATED : November 15, 2016
INVENTOR(S) : Jae Hong Kweon et al.

It is certified that error appears in the above-identified patent and that said Letters Patent is hereby corrected as shown below:

In the Claims

Column 22, Line 35:
"5. The method of claim 1, wherein $R_1$ are independently"

Should read:
--5. The method of claim 1, wherein $R_1$ and $R_2$ are independently--

Signed and Sealed this
Sixth Day of June, 2017

Michelle K. Lee
*Director of the United States Patent and Trademark Office*